(12) United States Patent
Medower et al.

(10) Patent No.: US 10,073,004 B2
(45) Date of Patent: Sep. 11, 2018

(54) DOE DEFECT MONITORING UTILIZING TOTAL INTERNAL REFLECTION

(71) Applicant: Apple Inc., Cupertino, CA (US)

(72) Inventors: Brian S. Medower, San Jose, CA (US); Meng Zhang, Sunnyvale, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 15/594,607

(22) Filed: May 14, 2017

(65) Prior Publication Data

US 2018/0080851 A1 Mar. 22, 2018

Related U.S. Application Data

(60) Provisional application No. 62/396,250, filed on Sep. 19, 2016.

(51) Int. Cl.
| | |
|---|---|
| *G01J 1/42* | (2006.01) |
| *G01M 11/02* | (2006.01) |
| *G01N 21/88* | (2006.01) |
| *G02B 5/18* | (2006.01) |
| *G02B 6/124* | (2006.01) |

(52) U.S. Cl.
CPC ..... *G01M 11/0207* (2013.01); *G01N 21/8806* (2013.01); *G02B 5/18* (2013.01); *G02B 6/124* (2013.01); *G01N 2201/061* (2013.01); *G02B 2005/1804* (2013.01)

(58) Field of Classification Search
CPC .. G01M 11/0207; G01M 11/02; G01J 1/0407; G01J 3/18; G02B 27/4205
USPC ................. 356/124–127, 213–218; 250/206; 359/565, 558, 569, 576
See application file for complete search history.

(56) References Cited

U.S. PATENT DOCUMENTS

| | | |
|---|---|---|
| 3,796,498 A | 3/1974 | Post |
| 4,180,702 A | 12/1979 | Sick et al. |
| | (Continued) | |

FOREIGN PATENT DOCUMENTS

| | | |
|---|---|---|
| CN | 1725042 A | 1/2006 |
| JP | 2008300106 | 12/2008 |
| | (Continued) | |

OTHER PUBLICATIONS

Fienup, J.R., "Phase Retrieval Algorithms: A Comparison", Applied Optics, vol. 21, No. 15, 12 pages, Aug. 1, 1982.

(Continued)

*Primary Examiner* — Hoa Pham
(74) *Attorney, Agent, or Firm* — D.Kligler IP Services Ltd.

(57) ABSTRACT

An optical apparatus includes a diffractive optical element (DOE), having at least one optical surface, a side surface, which is not parallel to the at least one optical surface of the DOE, and a grating, which is formed on the at least one optical surface so as to receive and diffract first radiation that is incident on the grating. The apparatus further includes at least one secondary radiation source, which is configured to direct second radiation to impinge on the side surface, causing at least part of the second radiation to propagate within the DOE while diffracting internally from the grating and to exit through the side surface. The apparatus also includes at least one radiation detector, which is positioned so as to receive and sense an intensity of the second radiation that has exited through the side surface.

16 Claims, 5 Drawing Sheets

(56) References Cited

U.S. PATENT DOCUMENTS

| | | | |
|---|---|---|---|
| 4,850,673 A | 7/1989 | Velzel et al. | |
| 5,406,543 A | 4/1995 | Kobayashi et al. | |
| 5,477,383 A | 12/1995 | Jain | |
| 5,606,181 A | 2/1997 | Sakuma et al. | |
| 5,648,951 A | 7/1997 | Kato et al. | |
| 5,691,989 A | 11/1997 | Rakuljic et al. | |
| 5,742,262 A | 4/1998 | Tabata et al. | |
| 5,781,332 A | 7/1998 | Ogata | |
| 6,002,520 A | 12/1999 | Hoch et al. | |
| 6,031,611 A | 2/2000 | Rosakis | |
| 6,462,874 B1 | 10/2002 | Soskind et al. | |
| 6,560,019 B2 | 5/2003 | Nakai | |
| 6,583,873 B1 | 6/2003 | Goncharov et al. | |
| 6,611,000 B2 | 8/2003 | Tamura et al. | |
| 6,664,998 B1 | 12/2003 | Kyoya et al. | |
| 6,707,027 B2 | 3/2004 | Liess et al. | |
| 6,927,852 B2 | 8/2005 | Reel | |
| 6,940,583 B2 | 9/2005 | Butt et al. | |
| 7,112,774 B2 | 9/2006 | Baer | |
| 7,149,030 B2 | 12/2006 | Kleemann et al. | |
| 7,227,618 B1 | 6/2007 | Bi | |
| 7,304,735 B2 | 12/2007 | Wang et al. | |
| 7,335,898 B2 | 2/2008 | Donders et al. | |
| 7,339,727 B1 | 3/2008 | Rothenberg et al. | |
| 7,443,587 B2 | 10/2008 | Dickson et al. | |
| 7,700,904 B2 | 4/2010 | Toyota et al. | |
| 7,952,781 B2 | 5/2011 | Weiss et al. | |
| 8,106,993 B2 | 1/2012 | Korenaga et al. | |
| 8,384,997 B2 | 2/2013 | Shpunt et al. | |
| 8,492,696 B2 | 7/2013 | Akerman et al. | |
| 8,630,039 B2 | 1/2014 | Shpunt | |
| 8,749,796 B2 | 6/2014 | Pesach et al. | |
| 8,829,406 B2 | 9/2014 | Akerman et al. | |
| 8,908,277 B2 | 12/2014 | Pesach et al. | |
| 9,528,906 B1 | 12/2016 | Yasovsky et al. | |
| 2004/0012958 A1 | 1/2004 | Hashimoto et al. | |
| 2004/0082112 A1 | 4/2004 | Stephens | |
| 2005/0178950 A1 | 8/2005 | Yoshida | |
| 2006/0001055 A1 | 1/2006 | Ueno et al. | |
| 2006/0252167 A1 | 11/2006 | Wang | |
| 2006/0252169 A1 | 11/2006 | Ashida | |
| 2006/0269896 A1 | 11/2006 | Liu et al. | |
| 2007/0019909 A1 | 1/2007 | Yamauchi et al. | |
| 2008/0042044 A1 | 2/2008 | Koyama | |
| 2008/0198355 A1 | 8/2008 | Domenicali et al. | |
| 2008/0212835 A1 | 9/2008 | Tavor | |
| 2008/0240502 A1 | 10/2008 | Freedman et al. | |
| 2008/0278572 A1 | 11/2008 | Gharib et al. | |
| 2009/0090937 A1 | 4/2009 | Park | |
| 2009/0096783 A1 | 4/2009 | Shpunt et al. | |
| 2009/0135487 A1* | 5/2009 | Ohmori | G02B 5/1809 359/569 |
| 2009/0183125 A1 | 7/2009 | Magal et al. | |
| 2009/0185274 A1 | 7/2009 | Shpunt | |
| 2010/0007717 A1 | 1/2010 | Spektor et al. | |
| 2010/0013860 A1 | 1/2010 | Mandella et al. | |
| 2010/0142014 A1 | 6/2010 | Rosen et al. | |
| 2010/0284082 A1 | 11/2010 | Shpunt et al. | |
| 2011/0091258 A1 | 1/2011 | Levola | |
| 2011/0069389 A1 | 3/2011 | Shpunt | |
| 2011/0187878 A1 | 8/2011 | Mor et al. | |
| 2011/0188054 A1 | 8/2011 | Petronius et al. | |
| 2011/0295331 A1 | 12/2011 | Wells et al. | |
| 2012/0038986 A1 | 2/2012 | Pesach | |
| 2012/0140109 A1 | 6/2012 | Shpunt et al. | |
| 2013/0127854 A1 | 5/2013 | Shpunt et al. | |
| 2013/0250387 A1 | 9/2013 | Chayat et al. | |
| 2014/0022348 A1 | 1/2014 | Shpunt | |
| 2014/0168260 A1* | 6/2014 | O'Brien | G09G 5/377 345/633 |
| 2017/0227416 A1* | 8/2017 | Chen | G01M 11/02 |
| 2018/0080851 A1* | 3/2018 | Medower | G01M 11/0207 |

FOREIGN PATENT DOCUMENTS

| | | |
|---|---|---|
| JP | 2011118178 | 6/2011 |
| WO | 9501558 A1 | 1/1995 |
| WO | 2007/043036 A1 | 4/2007 |
| WO | 2007/105205 A2 | 9/2007 |
| WO | 2008/120217 A2 | 10/2008 |
| WO | 2010/004542 A1 | 1/2010 |
| WO | 2012020380 A1 | 2/2012 |

OTHER PUBLICATIONS

Btendo, "Two Uni-axial Scanning Mirrors Vs One Bi-axial Scanning Mirror", Kfar Saba, Israel, 4 pages, Aug. 13, 2008.

Ezconn Czech A.S. "Site Presentation", 32 pages, Oct. 2009.

Gerchberg et al., "A Practical Algorithm for the Determination of the Phase from Image and Diffraction Plane Pictures," Optik 35, pp. 237-246, year 1972.

Sazbon et al., "Qualitative Real-Time Range Extraction for Preplanned Scene Partitioning Using Laser Beam Coding," Pattern Recognition Letters 26, pp. 1772-1781, year 2005.

Moharam et al. "Rigorous coupled-wave analysis of planar-grating diffraction", Journal of the Optical Society of America, vol. 71, No. 6, pp. 818-818, Jul. 1981.

Luxtera Inc., "Luxtera Announces World's First 10GBit CMOS Photonics Platform", Carlsbad, USA, 2 pages, Mar. 28, 2005 (press release).

Eisen et al., "Total internal reflection diffraction grating in conical mounting" ,Optical Communications 261, pp. 13-18, year 2006.

O'Shea et al., "Diffractive Optics: Design, Fabrication and Test", SPIE Tutorial Texts in Optical Engineering, vol. TT62, pp. 66-72, SPIE Press, USA 2004.

Microvision Inc., "Micro-Electro-Mechanical System (MEMS) Scanning Mirror", 1 page, years 1996-2009.

Garcia et al., "Three-dimensional mapping and range measurement by means of projected speckle patterns", Applied Optics, vol. 47, No. 16, pp. 3032-3040, Jun. 1, 2008.

Garcia et al.., "Projection of Speckle Patterns for 3D Sensing", Journal of Physics, Conference series 139, 7 pages, year 2008.

Bradley et al., "Synchronization and Rolling Shutter Compensation for Consumer Video Camera Arrays", IEEE International Workshop on Projector-Camera Systems—PROCAMS 2009, 8 pages, Miami Beach, Florida, 2009.

Marcia et al., "Fast Disambiguation of Superimposed Images for Increased Field of View", IEEE International Conference on Image Processing, San Diego, USA, 4 pages, Oct. 12-15, 2008.

U.S. Appl. No. # 15/352,624 office action dated Sep. 25, 2017.

International Application # PCT/US2017/039164 search report dated Oct. 20, 2017.

Prater et al., "Multilevel micro-structuring of glassy carbon for precision glass molding of diffractive optical elements", SPIE Proceedings, Advanced Fabrication Technologies for Micro/Nano Optics and Photonics VIII, vol. 3374, pp. 937410-1-937410-9, Mar. 13, 2015.

\* cited by examiner

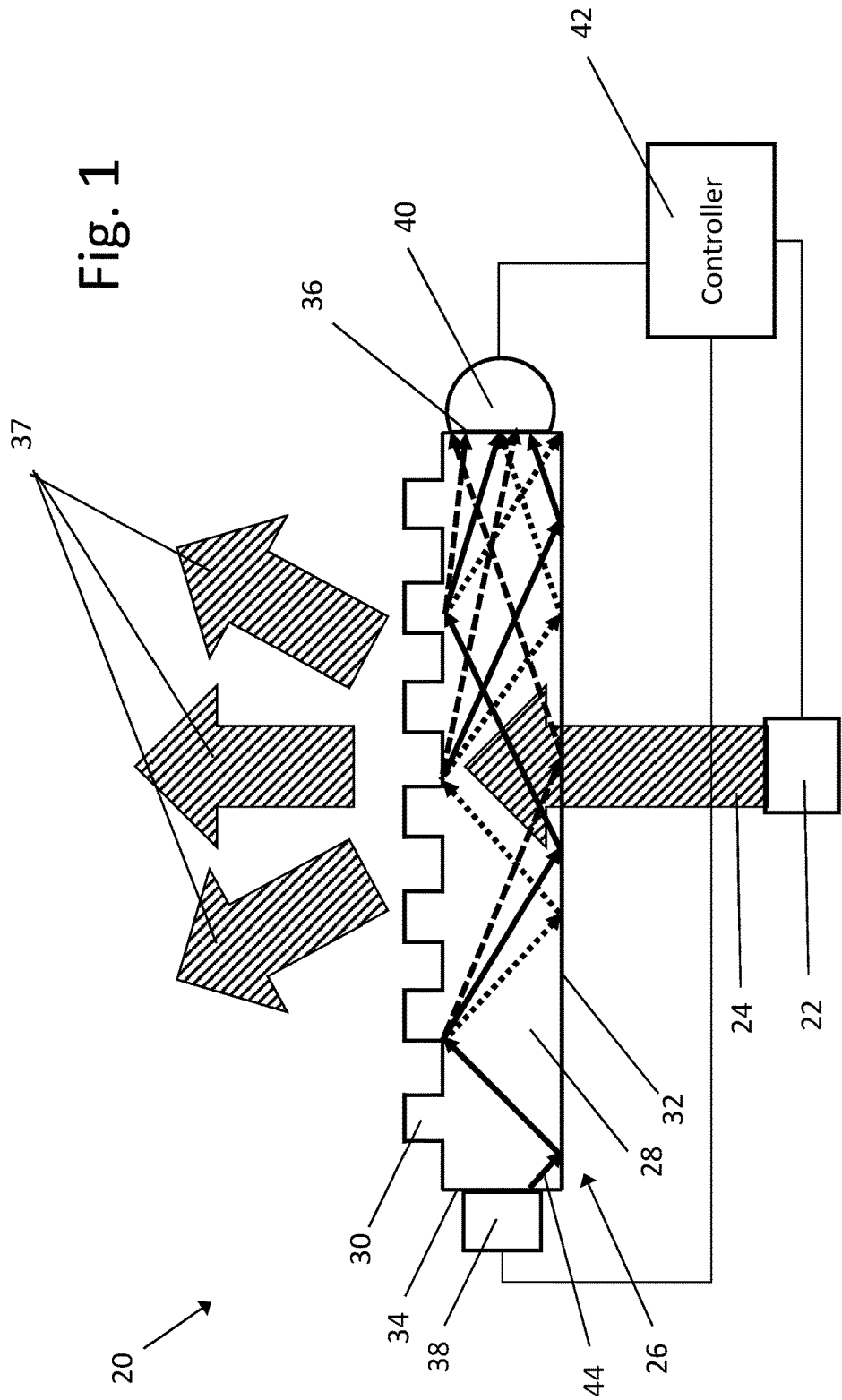

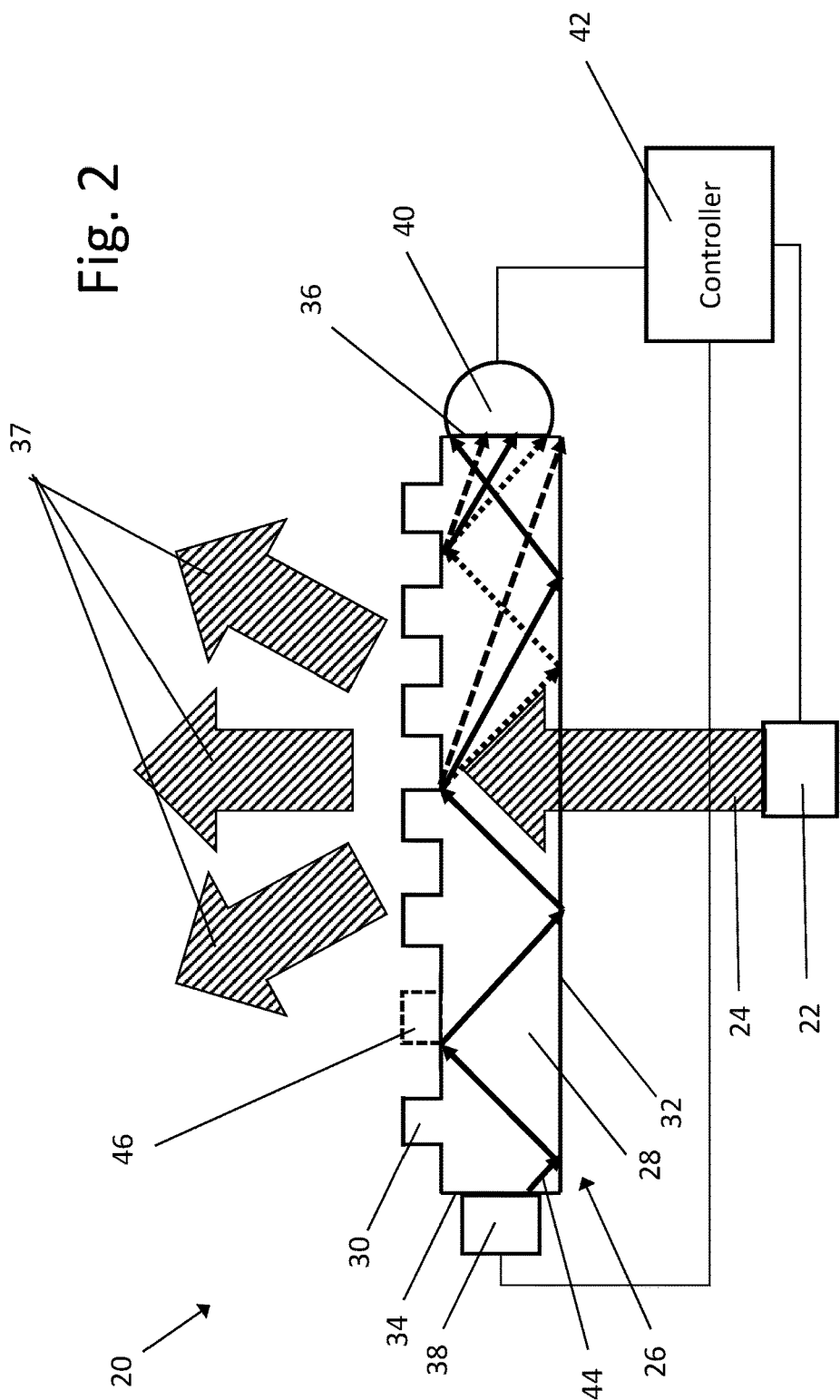

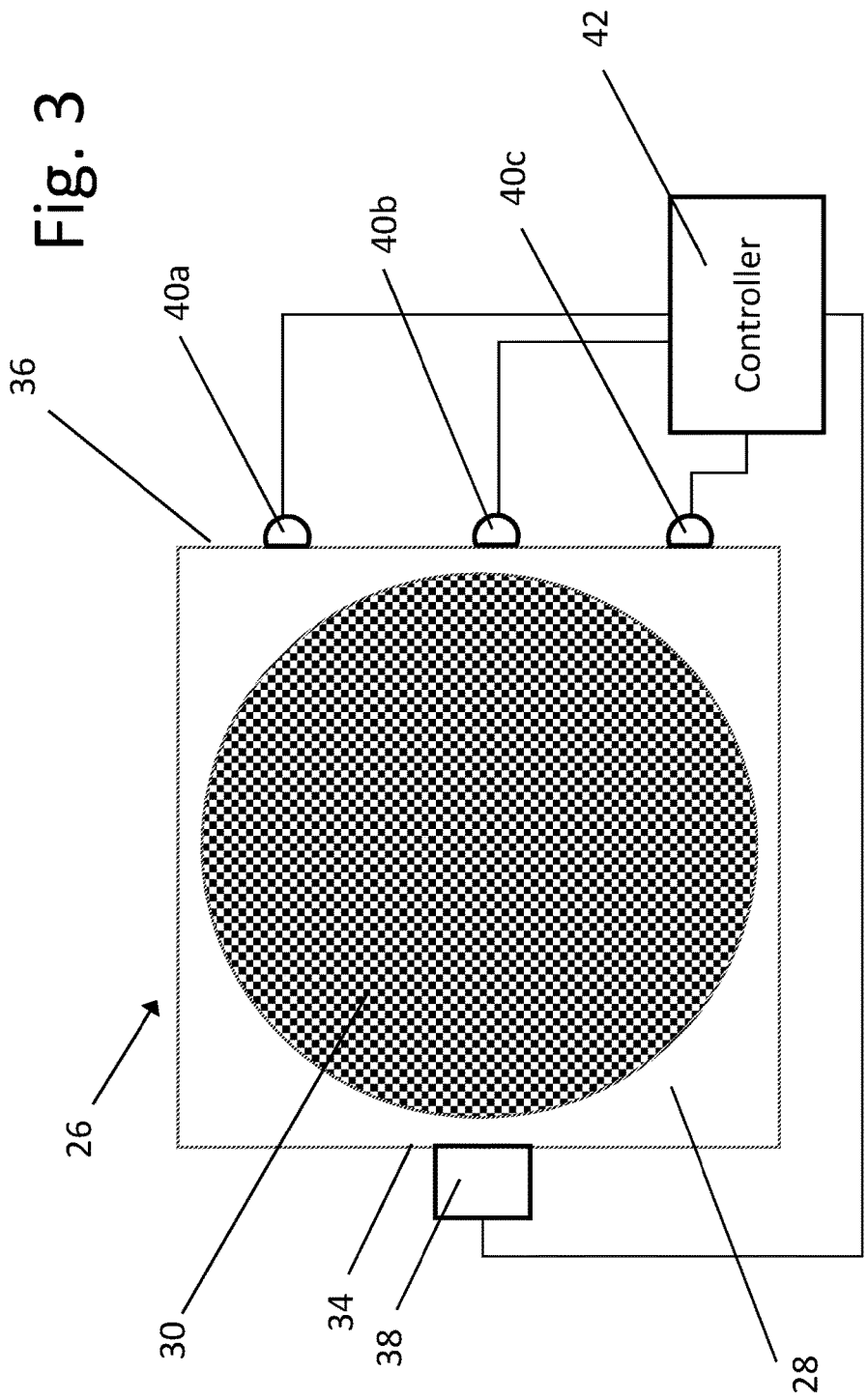

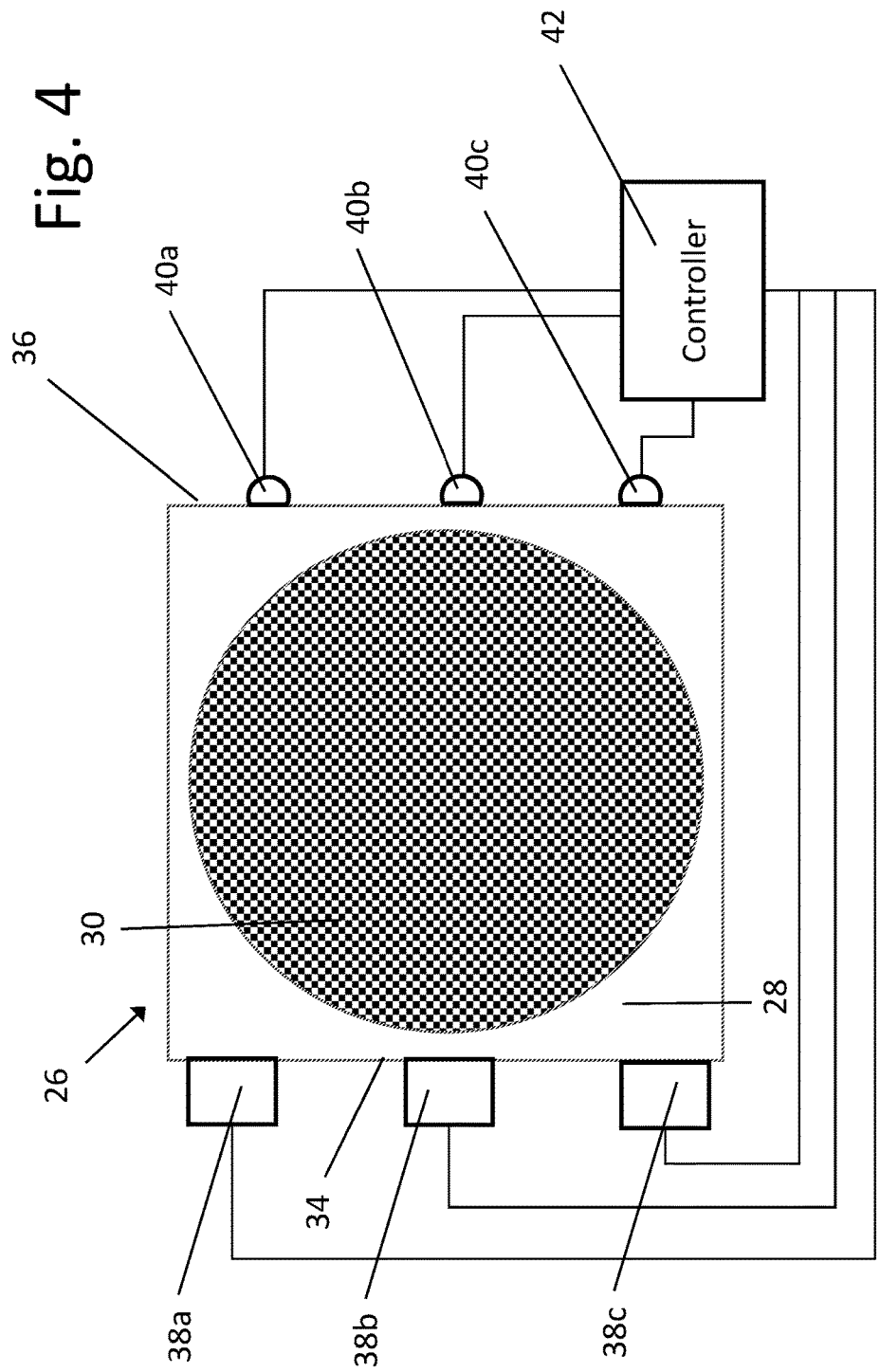

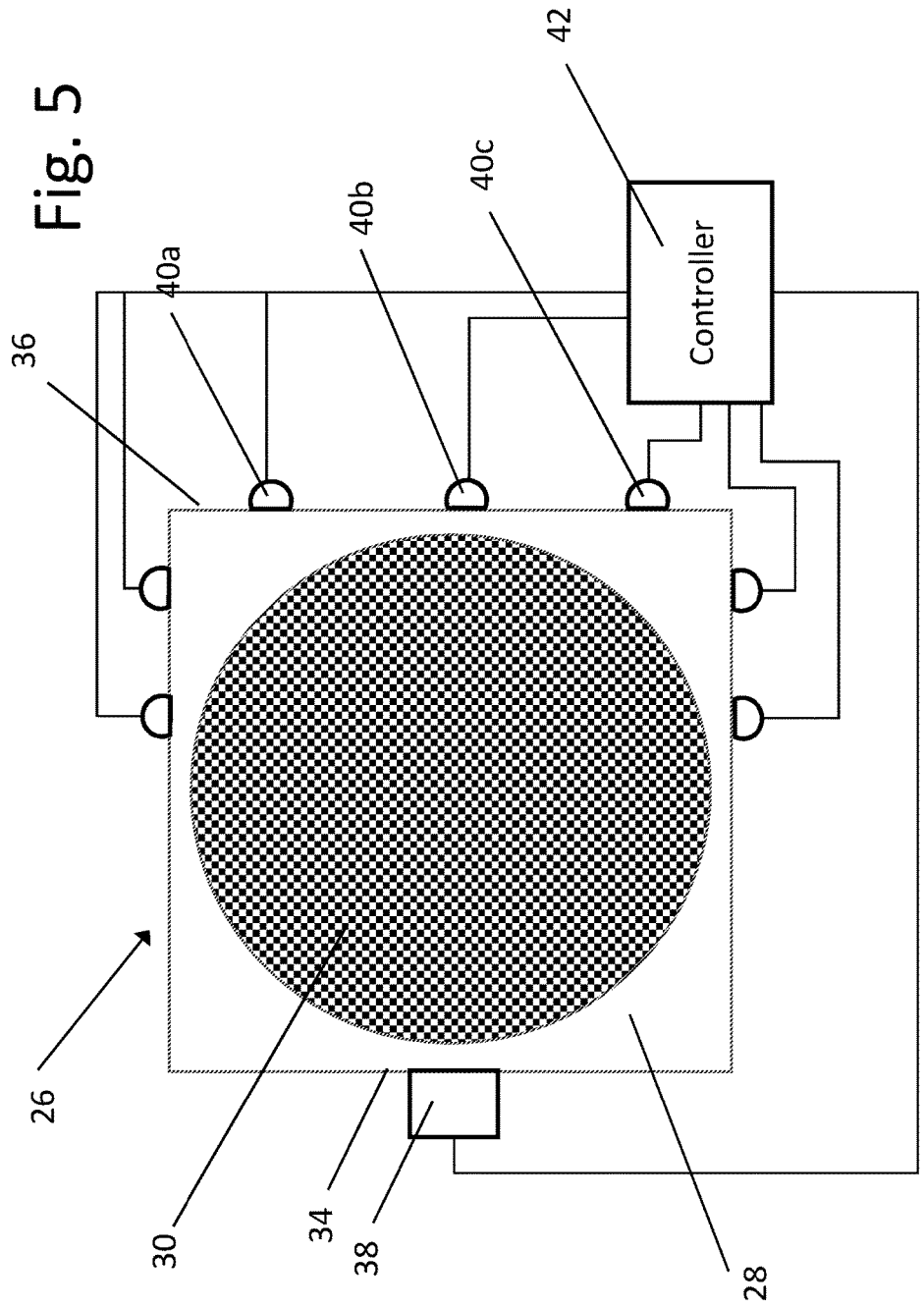

DOE DEFECT MONITORING UTILIZING TOTAL INTERNAL REFLECTION

CROSS-REFERENCE TO RELATED APPLICATION

This application claims the benefit of U.S. Provisional Patent Application 62/396,250, filed Sep. 19, 2016, which is incorporated herein by reference.

FIELD OF THE INVENTION

The present invention relates generally to diffractive optics, and specifically to monitoring defects in a diffractive optical element (DOE).

BACKGROUND

Diffractive optics are used in a wide variety of applications. In some applications, diffractive optical elements (DOEs) are used in creating a desired projection pattern, for purposes such as optical three-dimensional (3D) mapping, area illumination, and LCD backlighting. DOE-based projector designs are described, for example, in U.S. Patent Application Publication 2009/0185274, whose disclosure is incorporated herein by reference.

The "efficiency" of a DOE is a measure of the amount of input energy that the DOE diffracts, in relation to the energy of the incoming beam. This efficiency can vary in production due to manufacturing tolerances. It can also change during the lifetime and operation of the DOE for various reasons. For example, humidity and other vapors can condense on the DOE surface and lower its efficiency, or excess heat, due to a malfunction or misuse, can deform the DOE and change its efficiency. Such changes in efficiency can result in undesirable increases in the intensity of the zero diffraction order, which is not diffracted by the projection optics and may thus continue straight through the DOE to the projection volume.

U.S. Pat. No. 8,492,696, whose disclosure is incorporated herein by reference, describes a DOE-based projector with a built-in beam monitor, in the form of an integral optical detector. The detector signal can be continuously or intermittently monitored by a controller in order to evaluate the DOE efficiency and inhibit operation of the projector if the signal is outside a certain range.

SUMMARY

Embodiments of the present invention provide improved methods and devices for monitoring the performance of a DOE.

There is therefore provided, in accordance with an embodiment of the present invention, an optical apparatus, which includes a diffractive optical element (DOE), having at least one optical surface, a side surface, which is not parallel to the at least one optical surface of the DOE, and a grating, which is formed on the at least one optical surface so as to receive and diffract first radiation that is incident on the grating. The apparatus further includes at least one secondary radiation source, which is configured to direct second radiation to impinge on a first location on the side surface, causing at least part of the second radiation to propagate within the DOE while diffracting internally from the grating and to exit through at least one second location on the side surface. The apparatus also includes at least one radiation detector, which is positioned in proximity to the at least one second location so as to receive and sense an intensity of the second radiation that has exited through the side surface.

In a disclosed embodiment, the side surface is perpendicular to the at least one optical surface of the DOE.

In some embodiments, the at least one radiation detector includes a front surface that is in contact with the side surface of the DOE.

In further embodiments, the apparatus includes a controller, which is coupled to receive at least one signal from the at least one radiation detector that is indicative of the intensity of the second radiation that has exited through the side surface, and to monitor a performance of the DOE responsively to the at least one signal.

In some embodiments, the at least one radiation detector includes at least first and second radiation detectors, and the controller is coupled to receive first and second signals respectively from the first and second radiation detectors, and is configured to monitor the performance responsively to a difference between the first and second signals.

In other embodiments, the apparatus includes a primary radiation source, which is configured to direct the first radiation toward the at least one optical surface of the DOE, and the controller is coupled to control an operation of the primary radiation source responsively to the monitored performance.

In further embodiments, the controller is configured to inhibit the operation of the primary radiation source when the at least one signal is outside a predefined range.

In still further embodiments, the grating is configured to direct the first radiation into multiple orders of diffraction, and a change of the at least one signal is indicative of an increase of an intensity of a zero order of the diffraction. The controller is configured to inhibit the operation of the primary radiation source when the change exceeds a predefined threshold.

In some embodiments, the primary radiation source and the at least one secondary radiation source are configured to emit the first and second radiation, respectively, at different, respective wavelengths.

There is also provided, in accordance with an embodiment of the present invention, an optical method, which includes positioning a diffractive optical element (DOE), having at least one optical surface on which a grating is formed and a side surface, which is not parallel to the at least one optical surface, to receive and diffract first radiation that is incident on the grating. Second radiation is directed to impinge on a first location on the side surface, causing at least part of the second radiation to propagate within the DOE while diffracting internally from the grating and to exit through at least one second location on the side surface. An intensity of the second radiation that has exited through the side surface is received and sensed. In one embodiment, performance of the DOE is monitored responsively to at least one signal indicative of the intensity of the second radiation that has exited through the side surface.

The present invention will be more fully understood from the following detailed description of the embodiments thereof, taken together with the drawings in which:

BRIEF DESCRIPTION OF THE DRAWINGS

FIGS. 1-2 are a schematic side views of an optical projector with a beam monitor, in accordance with an embodiment of the present invention; and FIGS. 3-5 are schematic top views of a DOE with beam monitors, in accordance with further embodiments of the present invention.

DETAILED DESCRIPTION OF EMBODIMENTS

Optical projectors based on diffractive optical elements (DOEs) sometimes pass substantial zero-order radiation, as described in the above-mentioned US 2009/0185274: A portion of the input beam of the projector (the zero diffraction order) may not be diffracted by the projection optics and may thus continue through to the projection volume. Changes in efficiency of a DOE, with concomitant increases in the zero-order intensity, can compromise system performance and may have various other undesirable consequences.

Any DOE comprises multiple optical surfaces, including at least an entrance surface and an exit surface. The diffractive effect of the DOE is provided by a grating formed on one of these optical surfaces (which may be the entrance surface, the exit surface, or an internal surface within the DOE), or by multiple gratings on multiple optical surfaces. Such gratings may have any suitable shape and form, depending on the diffraction pattern that the DOE is to create. The gratings receive first radiation, emitted by a primary radiation source, entering the DOE via the entrance surface and diffract the first radiation into a predefined pattern comprising multiple diffraction orders that exit the DOE via the exit surface.

The diffraction efficiency of each of the gratings of the DOE may be affected by a local defect, such as, for example, a mechanical deformation (scratch, pit, local grating erasure), contamination, or condensation. This change of diffraction efficiency may cause or contribute to an increase in the amount of zero-order radiation passed by the DOE and may cause other changes in the powers of the diffracted orders of the DOE. For ensuring proper operation of an optical projector based on a DOE, real-time monitoring of the performance of the grating of the DOE is highly desirable.

Embodiments of the present invention that are described hereinbelow enable robust, real-time monitoring of the performance of a DOE, using only minimal additional hardware, which can be implemented with only minimal impact on the size and cost of the overall DOE assembly. Furthermore, these embodiments enable the monitoring to take place without interfering with the functioning of an optical projector in which the DOE is incorporated. In the description that follows, it is assumed that a primary radiation source in such a projector directs first radiation of a certain wavelength through the optical surfaces of the DOE, to be diffracted by the grating.

In the disclosed embodiments, a secondary radiation source, such as an LED (Light Emitting Diode) or a laser, is positioned in proximity to a first location on a side surface of the DOE so as to send second radiation into the DOE. (The term "side surface" in the present description and in the claims refers to a surface of the DOE that is not parallel to the optical surfaces and is outside the path of the intended diffraction pattern. The side surface may comprise one or multiple segments, depending on the shape of the DOE.) One or more radiation detectors are positioned in proximity to a second location on the side surface, for example a location opposite to the first location, so as to receive and sense the second radiation that has propagated within the DOE.

The second radiation that has entered the DOE typically comprises multiple rays (or directions of propagation), either as a continuous or a discrete angular spectrum. This second radiation will propagate within the DOE as a combination of total internal reflection and diffraction from the point where it entered the DOE through the first location on the side surface until it reaches the second location on the side surface and exits from the DOE. For the propagation of the second radiation, the DOE functions as a slab waveguide. The distance and coupling of the secondary radiation source to the DOE may be used for optimizing the coupling efficiency into totally internally reflected propagation, as well as for optimizing the uniformity of illumination of the grating. The source distance and coupling may also be used for achieving high internal diffraction efficiency for rays that continue propagating with total internal reflection, and low internal diffraction efficiency for rays that do not satisfy the condition for total internal reflection, i.e., that would "leak" out of the DOE.

During its propagation within the DOE, the second radiation probes the integrity of the DOE in real-time, as the composition of rays of the second radiation is influenced by any defects on the optical surfaces of the DOE. This influence of defects manifests itself in the second radiation impinging on the radiation detectors, both as a change in the total power and as a change in the spatial distribution of the irradiance.

Although a single detector of the second radiation can be sufficient, using several detectors enables the sensing of changes in the spatial distribution of the irradiance exiting the DOE. It also enables differential measurements between pairs of detectors, reducing the effects of fluctuations in the power level of the secondary radiation source as well as the influence of minor changes in optical alignment of the secondary radiation source and radiation detectors.

The diameters of the secondary radiation source as well as the radiation detectors are typically smaller than the thickness of the DOE; in some embodiments these components are cemented onto the side surface of the DOE both for a compact and robust assembly and for good optical coupling into the DOE.

In some embodiments, the spectrum of the secondary radiation source is chosen to be different from that of the first radiation, i.e., the primary radiation source has a first transmission spectrum, while the secondary radiation source has a second transmission spectrum different from the first. Appropriate spectral filtering for detectors receiving the first radiation from the optical projector and for the radiation detectors monitoring the DOE performance can be used in reducing crosstalk between the first radiation and the second radiation, thus preventing interference between the DOE monitor and the optical projector. In some embodiment, the first and second transmission spectra are chosen to be non-overlapping, and the radiation incident on the radiation detectors monitoring the DOE performance is filtered by a filter that filters the first transmission spectrum and lets pass at least a portion of the second transmission spectrum. This spectral arrangement is useful particularly in simultaneous testing and pattern projection.

Additionally or alternatively, the present embodiments can be used in combination with other approaches. For example, the detectors can be used to measure natural total internal reflection within the DOE from the primary source when the secondary source is not on. Alternatively, when the first and second transmission spectra are different, one or more detectors can be used to monitor the secondary source while one or more other detectors monitor total internal reflection from the primary source.

Using a secondary radiation source, which is independent of the primary radiation source, brings the additional benefits of being able to monitor the DOE without even turning the primary radiation source on. Thus, the DOE can be monitored without the power consumption associated with the primary radiation source, which is typically of higher power than the secondary radiation source. Moreover, in case there is a suspicion of damage having been inflicted to the DOE by an adverse event (e.g., dropping the optical projector), the status of the DOE can be verified without turning the primary radiation source on.

In some embodiments, a controller receives signals from the radiation detectors that are indicative of changes in the diffraction efficiency of the grating of the DOE, and thus monitors the performance of the DOE. Based on these signals, the controller may control the operation of the primary radiation source and may inhibit the operation of the primary radiation source when the signals are outside a predefined range.

As an example, consider a grating that has been "smoothed out" due to a partial erasure of the grating profile. A grating with a lower profile typically has a lower diffraction efficiency, reducing the diffraction of the first radiation, and thus increasing the intensity of the zero order. By the same token, the internal diffraction losses experienced by the second radiation are reduced, i.e., the second radiation experiences reduced diffraction near the defect area and increases the zero order/total internal reflection intensity. Consequently, the intensity of the probe signal is increased. In such a case, the controller would interpret the reduction of internal diffraction losses of the second radiation as indicating a likely increase in the intensity of the zero-order of the first radiation. The controller would now typically inhibit the operation of the radiation source when the signal changes by more than a certain threshold, possibly by simply turning the radiation source off.

FIG. 1 is a schematic side view of an optical projector 20 with a DOE monitor, in accordance with an embodiment of the present invention. A primary radiation source 22 emits a beam 24 of first radiation toward a DOE 26. Typically, the radiation is coherent optical radiation in the visible, infrared or ultraviolet range (the spectral regions that are generally referred to as "light"). Primary radiation source 22 may comprise a laser diode, for example, or an array of laser diodes, such as a vertical-cavity surface-emitting laser (VCSEL) array.

DOE 26 comprises a transparent substrate 28, such as glass or a suitable plastic, for example polycarbonate, with a grating 30 formed on one of its optical surfaces. In the pictured example, grating 30 is formed on the exit surface of DOE 26, away from radiation source 22, with beam 24 entering DOE 26 through an entrance surface 32. DOE 26 further comprises a side surface, comprising side surface segments 34 and 36. (The other side surface segments are not shown in this figure. The multiple side surface segments together make up the side surface of DOE 26, although a circular DOE, for example, will have a side surface comprising only a single segment.) In the illustration of FIG. 1, the dimensions (width and height) of DOE 26, as well as the period and amplitude of grating 30, are not to the same scale.

DOE 26 generates from beam 24 a pattern comprising zero and first diffraction orders 37, which exit DOE 26 from grating 30. In other embodiments, patterns comprising other diffraction orders, including two-dimensional diffraction patterns, may be generated. Alternatively or additionally, as noted earlier, DOE 26 may comprise one or more gratings formed on entrance surface 32 or on one or more internal optical surfaces (not shown). The gratings may be configured, for example, to generate multiple, adjacent instances of a pattern of spots, as described in U.S. Pat. No. 8,384,997, whose disclosure is incorporated herein by reference. Such patterns are useful particularly in 3D mapping (in association with an imaging assembly), as described in U.S. Pat. No. 8,384,997 and in the above-mentioned U.S. Pat. No. 8,492,696.

Defects of DOE 26 are monitored using a secondary radiation source 38, for example an LED or a laser diode, and one or more radiation detectors 40, for example photodiodes. Both secondary radiation source 38 and radiation detectors 40 are connected to a controller 42. Controller 42 is also connected to primary radiation source 22.

Although only a single radiation source 38 and a single radiation detector 40 are shown in FIGS. 1 and 2, alternative embodiments of the present invention may use any number of radiation sources and detectors, such as one, two, three, four, or more radiation detectors. The detectors may be mounted one above the other (along the vertical axis in FIGS. 1 and 2) and/or distributed along the side surface of the DOE, as illustrated in FIGS. 3-5. Due to their small sizes, secondary radiation sources 38 and radiation detectors 40 (or possible additional radiation detectors) will have only a small impact on the size of optical projector 20. In some embodiments, the emission spectrum of secondary radiation source 38 is chosen to be separate from that of primary radiation source 22, thus—by employing suitable spectral filtering—avoiding any impact of the second radiation on the functioning of optical projector 20.

As primary radiation source 22 and secondary radiation source 38 are completely independent from each other, the latter can be used for monitoring DOE 26 while the former is turned off. This mode of operation is advantageous for saving power in a portable device. It also permits monitoring DOE 26 without presence of the first radiation, especially after an adverse event, such as, for example, a mechanical shock to optical projector 20.

Secondary radiation source 38 is positioned on side surface segment 34 so as to emit a second radiation 44 into DOE 26 through side surface segment 34. For the sake of clarity, second radiation 44 is illustrated using a single ray, although second radiation 44 that has entered DOE 26 typically comprises multiple directions of rays, either as a continuous or a discrete angular spectrum. The direction of second radiation 44 is also configured, by a suitable choice of secondary radiation source 38 and the orientation of its radiation pattern, so that it reflects from entrance surface 32 by total internal reflection. For example, in a polycarbonate substrate with index of refraction n=1.57, the minimum angle for total internal reflection is 39.5°, so that second radiation 44 with an angle of incidence on entrance surface 32 above 39.5° fulfills the condition for total internal reflection.

The propagation of second radiation 44 across DOE 26 towards side surface 36 takes place through a combination of multiple occurrences of total internal reflection and diffraction. This will become clear to the observer by following the arrow indicating second radiation 44 (solid line). At each point where second radiation 44 impinges on entrance surface 32, it is reflected by total internal reflection. At each point where second radiation 44 impinges on grating 30, some of it diffracts into higher (non-zero) orders, shown as dotted lines, whereas the remaining part of second radiation 44 is reflected by total internal reflection (equivalent to the zero diffracted order). The higher diffracted orders again reflect from entrance surface 32 by total internal reflection. This process of diffraction and total internal reflection continues throughout the width of DOE 26, with second radiation 44 probing both grating 30 and entrance surface 32, until reflected and diffracted second radiation 44 impinges on side surface segment 36.

The distance and coupling of secondary radiation source 38 into side surface segment 34 may be optimized to provide uniform illumination on grating 30 by second radiation 44. The optimization can further be used to achieve a high internal diffraction efficiency from grating 30 for diffracted modes propagating within DOE 26 and a low diffraction efficiency for diffracted modes that would not be totally internally reflected, i.e. that would "leak" out of DOE 26.

Typically, side surface segment 36 is transparent and perpendicular to the optical surfaces of DOE 26, permitting second radiation 44 to exit through the side surface. Alternatively, reflected and diffracted second radiation 44 may exit through a light-transmitting side surface oriented at any suitable angle that is not parallel to the optical surfaces.

Radiation detectors 40 receive and sense respective portions of second radiation 44 that exits DOE 26 through side surface segment 36. In the pictured embodiment, the front surfaces of radiation detectors 40 are fixed to be in contact with side surface segment 36 of DOE 26. Using more than one radiation detector enables sensing a spatial profile of second radiation 44 at the side surface and utilizing the additional information in the spatial profile for monitoring DOE 26. More than one radiation detector also enables differential sensing of the signals from the detectors. This, in turn, reduces the sensitivity of the sensing to common-mode variations of the signals, such as power fluctuations of second radiation source 38, as well as the sensitivity to a minor misalignment of second radiation source 38 and radiation detectors 40.

Controller 42 monitors the signals from radiation detectors 40, which are indicative of the efficiency of grating 30. Should grating 30 be degraded or fail entirely, the intensities of reflected and diffracted second radiation 44 will be affected, and the signals output by radiation detectors 40 will change accordingly.

If the signal is outside a certain permitted range, and particularly if the signal changes by more than a certain threshold—either dropping below a predefined minimum level or exceeding a predefined maximum—controller 42 will inhibit the operation of primary radiation source 22, and may simply turn off the primary radiation source entirely. In this manner, controller 42 indirectly monitors the intensity of the zero diffraction order from first radiation, which becomes stronger as the grating efficiency degrades, and by virtue of this monitoring is able to prevent the operation of optical projector 20 outside its normal balance between diffracted orders 37. To perform the above functions, controller 42 may comprise, for example, an embedded microcontroller or even a simple threshold-sensing logic device, which may be integrated with optical projector 20. Alternatively, the functions of controller 42 may be performed by a microprocessor, which also performs other functions in a system in which optical projector 20 is integrated.

FIG. 2 is a schematic side view of optical projector 20, in accordance with an embodiment of the present invention, showing the effect of removing a period 46 of grating 30 (mimicking local erasure of grating 30). Due to the local erasure of period 46, no diffraction of second radiation 44 takes place at that location. This absence of diffraction changes the balance between undiffracted and diffracted second radiation 44 at side surface 36 as compared to FIG. 1, and consequently changes the balance between the signals from radiation detectors 40. This changed balance will be detected by controller 42, and may, in case the change exceeds a given limit, cause controller 42 to inhibit the operation of primary radiation source 22.

FIG. 3 is a schematic top view of DOE 26 with a beam monitor, in accordance with another embodiment of the present invention. DOE 26 comprises grating 30 on top of substrate 28, entrance surface 32 (not shown in this figure), and four side surface segments, of which the relevant ones for the present description are segments 34 and 36. As in FIGS. 1-2, secondary radiation source 38 and radiation detectors 40 are attached to side surface segments 34 and 36, respectively. In the view shown in FIG. 3, however, separate radiation detectors 40a-c are shown, aligned along the length of side surface segment 36, with radiation detector 40b located in the middle of side surface segment 36 and the remaining two detectors located towards the corners of substrate 28, symmetrically with respect to radiation detector 40b. Controller 42 is connected to secondary radiation source 38, to radiation detectors 40a-c, and to primary radiation source 22 (not shown).

In FIG. 3, by way of example, detectors 40a-c are positioned symmetrically with respect to radiation source 38 and are positioned in the middle and the corners of segment 36. Neither of these features is mandatory, but rather, source 38 and detectors 40 may be placed in any manner appropriate in various different locations. Additionally, although each detector in theory samples light from all portions of DOE 26, a given detector 40 will be more sensitive to defects that occur along or near the optical path between source 38 and the detector. For enhanced detection, it may be desirable to have a certain number of detectors and/or have the detectors take up a certain percentage of the lateral area of the one or more side surfaces.

Radiation source 38 in FIG. 3 takes up only a subset of the width of the DOE, which may possibly result in non-uniform radiation transmission across the grating. In some instances, it may be desirable to have the width of the radiation source be at least the width of the grating. In other instances, it may be desirable to have multiple individually-addressable radiation sources.

FIG. 4 is a schematic top view of DOE 26 with this latter sort of beam monitor, in accordance with yet another embodiment of the present invention. Multiple radiation sources 38a-c in this embodiment may be illuminated simultaneously or sequentially. In the present example with three sources, activating radiation source 38a may help facilitate detection of defects in the left side of DOE 26; activating radiation source 38b may facilitate detections in the middle portion of the DOE, etc. (It should be appreciated, however, that it may be still be possible to detect defects at one side of the DOE while the source at the other side is activated.)

FIG. 5 is a schematic top view of DOE 26 with a beam monitor, in accordance with still another embodiment of the present invention in which detectors 40 are positioned on multiple different segments of side surface 36 of the DOE. This approach can increase the sensitivity of detecting defects on different portions of the gratings, depending on detector placement. While shown in this figure as being positioned on three side segments of DOE 26, detectors 40 can alternatively be positioned on two sides, or more sides (depending on how many side surface segments the DOE has).

In other embodiments (not shown in the figures), DOE 26 may have both emitters on multiple side surface segments and detectors on multiple side surface segments. Each surface segment may have only emitters or only detectors, as in the embodiments shown above. Alternatively, one or more surfaces may have both emitters and detectors positioned thereon, in symmetric or non-symmetric arrangements. (References herein to placing emitters and detectors "on" a side surface segment should be understood to mean that the emitters transmit radiation through and the detectors receive radiation from the side surface, but without necessarily being in direct physical contact with the side surface.)

In some embodiments of the present invention (not shown in the figures), secondary radiation sources and detectors, as described above, are applied to multiple stacked DOEs, such as in the arrangements shown in the above-mentioned U.S. Patent Application Publication 2009/0185274. In such embodiments, there may be a separate testing apparatus, with secondary radiation sources and detectors, for each individual DOE. In some instances, the secondary radiation source for one DOE may have the same emission spectrum as the secondary radiation source for the other DOE, or they may have different emission spectra. In some of these instances, the DOEs can be checked in a time-multiplexed manner (e.g., to reduce cross-talk between the two DOEs). In other instances, the DOEs may be checked simultaneously. For example, in instances in which the radiation sources have different emission spectra, the detectors for one DOE may be selectively-sensitive to certain wavelengths (e.g., via a filter) outside the spectrum of the other DOE, and vice versa. The radiation sources and detectors may be positioned on the same sides of the two DOEs, or they may be placed in different detection arrangements in any appropriate relative orientations.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Optical apparatus, comprising:
a diffractive optical element (DOE), comprising:
at least one optical surface;
a side surface, wherein the side surface is not parallel to the at least one optical surface of the DOE; and
a grating, which is formed on the at least one optical surface so as to receive and diffract first radiation that is incident on the grating;
at least one radiation source, which is configured to direct second radiation to impinge on a first location on the side surface, causing at least part of the second radiation to propagate within the DOE while diffracting internally from the grating and to exit through at least one second location on the side surface; and
at least one radiation detector, which comprises a front surface that is in contact with the side surface of the DOE and is positioned in proximity to the at least one second location so as to receive and sense an intensity of the second radiation that has exited through the side surface.

2. The apparatus according to claim 1, wherein the side surface is perpendicular to the at least one optical surface of the DOE.

3. The apparatus according to claim 1, and comprising a controller, which is coupled to receive at least one signal from the at least one radiation detector that is indicative of the intensity of the second radiation that has exited through the side surface, and to monitor a performance of the DOE responsively to the at least one signal.

4. The apparatus according to claim 3, wherein the at least one radiation detector comprises at least first and second radiation detectors, and wherein the controller is coupled to receive first and second signals respectively from the first and second radiation detectors, and is configured to monitor the performance responsively to a difference between the first and second signals.

5. The apparatus according to claim 3, and comprising a primary radiation source, which is configured to direct the first radiation toward the at least one optical surface of the DOE, wherein the controller is coupled to control an operation of the primary radiation source responsively to the monitored performance.

6. The apparatus according to claim 5, wherein the controller is configured to inhibit the operation of the primary radiation source when the at least one signal is outside a predefined range.

7. The apparatus according to claim 5, wherein the primary radiation source and the at least one radiation source are configured to emit the first and second radiation, respectively, at different, respective wavelengths.

8. Optical apparatus, comprising:
a diffractive optical element (DOE), comprising:
at least one optical surface;
a side surface, wherein the side surface is not parallel to the at least one optical surface of the DOE; and
a grating, which is formed on the at least one optical surface so as to receive and diffract first radiation that is incident on the grating;
a primary radiation source, which is configured to direct the first radiation toward the at least one optical surface of the DOE;
at least one secondary radiation source, which is configured to direct second radiation to impinge on a first location on the side surface, causing at least part of the second radiation to propagate within the DOE while diffracting internally from the grating and to exit through at least one second location on the side surface;
at least one radiation detector, which is positioned in proximity to the at least one second location so as to receive and sense an intensity of the second radiation that has exited through the side surface; and
a controller, which is coupled to receive at least one signal from the at least one radiation detector that is indicative of the intensity of the second radiation that has exited through the side surface, and to monitor a performance of the DOE responsively to the at least one signal,
wherein the grating is configured to direct the first radiation into multiple orders of diffraction, and wherein a change of the at least one signal is indicative of an increase of an intensity of a zero order of the diffraction, and the controller is configured to inhibit the operation of the primary radiation source when the change exceeds a predefined threshold.

9. An optical method, comprising:
positioning a diffractive optical element (DOE), having at least one optical surface on which a grating is formed and a side surface, wherein the side surface is not parallel to the at least one optical surface, to receive and diffract first radiation that is incident on the grating;
directing second radiation to impinge on a first location on the side surface, causing at least part of the second radiation to propagate within the DOE while diffracting internally from the grating and to exit through at least one second location on the side surface; and receiving and sensing an intensity of the second radiation that has exited through the side surface using a radiation detector having a front surface that is in contact with the side surface of the DOE.

10. The method according to claim 9, wherein the side surface is perpendicular to the at least one optical surface of the DOE.

11. The method according to claim 9, wherein receiving and sensing the intensity comprises monitoring a performance of the DOE responsively to at least one signal indicative of the intensity of the second radiation that has exited through the side surface.

12. The method according to claim 11, wherein the at least one signal comprises at least a first and a second signal, and wherein monitoring the performance of the DOE comprises monitoring the performance responsively to a difference between the first and second signals.

13. The method according to claim 11, and comprising directing the first radiation from a primary radiation source toward the at least one optical surface of the DOE, and comprising controlling an operation of the primary radiation source responsively to the monitored performance.

14. The method according to claim 13, wherein controlling the operation of the primary radiation source comprises inhibiting the operation when the at least one signal is outside a predefined range.

15. The method according to claim 14, wherein the grating is configured to direct the first radiation into multiple orders of diffraction, and wherein a change of the at least one signal is indicative of an increase of an intensity of a zero order of the diffraction, and wherein controlling the operation of the primary radiation source comprises inhibiting the operation when the change exceeds a predefined threshold.

16. The method according to claim 13, wherein the first radiation and the second radiation are emitted at different, respective wavelengths.

* * * * *